United States Patent [19]

Ferragamo et al.

[11] Patent Number: 4,863,426
[45] Date of Patent: Sep. 5, 1989

[54] PERCUTANEOUS VENOUS CATHETER

[76] Inventors: Michael C. Ferragamo, 2355 Old Wellington St., North Dighton, Mass. 02764; Per Troein, 5 Aylward La., Foxboro, Mass. 02035

[21] Appl. No.: 86,515

[22] Filed: Aug. 18, 1987

[51] Int. Cl.⁴ .............................................. A61M 11/00
[52] U.S. Cl. ...................................... 604/93; 604/175; 604/282
[58] Field of Search .................... 604/93, 96, 282, 175, 604/265, 180, 280, 97, 98, DIG. 26, 122, 891.1, 892.1, 283, 171, 172, 174, 8–10; 128/DIG. 24

[56] References Cited

U.S. PATENT DOCUMENTS

| | | | |
|---|---|---|---|
| 3,486,234 | 12/1969 | Stevens | 604/282 |
| 3,498,286 | 3/1970 | Polanyi et al. | 604/282 |
| 3,633,585 | 1/1972 | McDonald, Jr. | 604/8 |
| 3,699,956 | 10/1972 | Kitrilakis et al. | 604/175 |
| 3,752,162 | 8/1973 | Newash | 604/93 |
| 3,889,685 | 6/1975 | Miller, Jr. et al. | 604/96 |
| 4,054,139 | 10/1977 | Crossley | 604/265 |
| 4,329,992 | 5/1982 | Becker et al. | 128/DIG. 24 |
| 4,349,022 | 9/1982 | Ishikawa | 604/180 |
| 4,488,877 | 12/1984 | Klein et al. | 604/175 |
| 4,489,722 | 12/1984 | Ferraro et al. | 604/96 |
| 4,668,225 | 5/1987 | Russo et al. | 604/93 |
| 4,676,782 | 6/1987 | Yamamoto et al. | 604/175 |
| 4,723,947 | 2/1988 | Konopka | 604/283 |

FOREIGN PATENT DOCUMENTS

| | | | |
|---|---|---|---|
| 0010865 | 5/1980 | European Pat. Off. | 604/175 |
| 3239032 | 4/1984 | Fed. Rep. of Germany | 604/282 |

Primary Examiner—John D. Yasko

[57] ABSTRACT

A percutaneous venous catheter includes a first fluid-pervious segment for implantation in the body and a second extravascular segment composed of a flexible tube surrounded by a vapor-barrier sheath. A cuff marks the boundary between the two segments and a connector fitting is mounted to the free end of the extravascular segment, there being a continuous fluid path between the fitting and the tip. The vapor barrier present in the extravascular segment of the catheter prevents fluid transpiration through the catheter wall that tends to draw fluid along the catheter causing an occluding thrombus formation at the catheter tip.

8 Claims, 1 Drawing Sheet

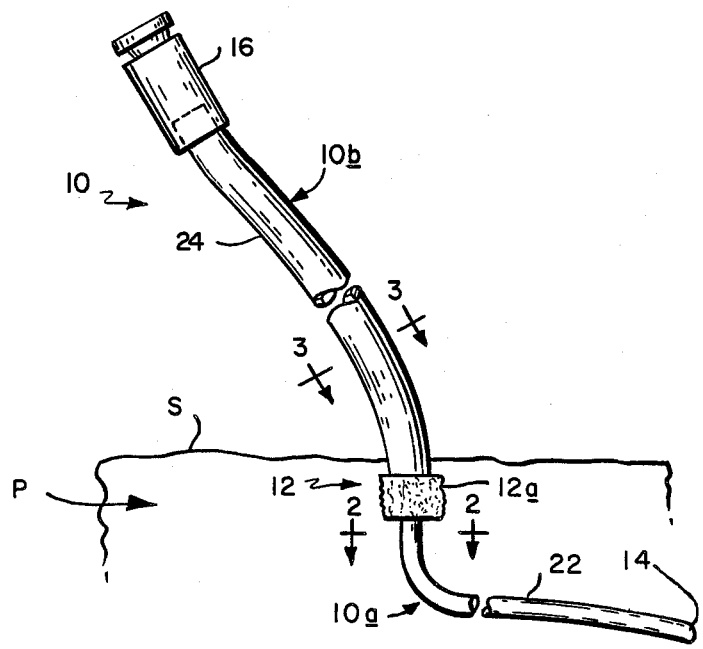
FIG. 1
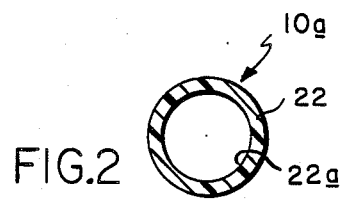
FIG. 2
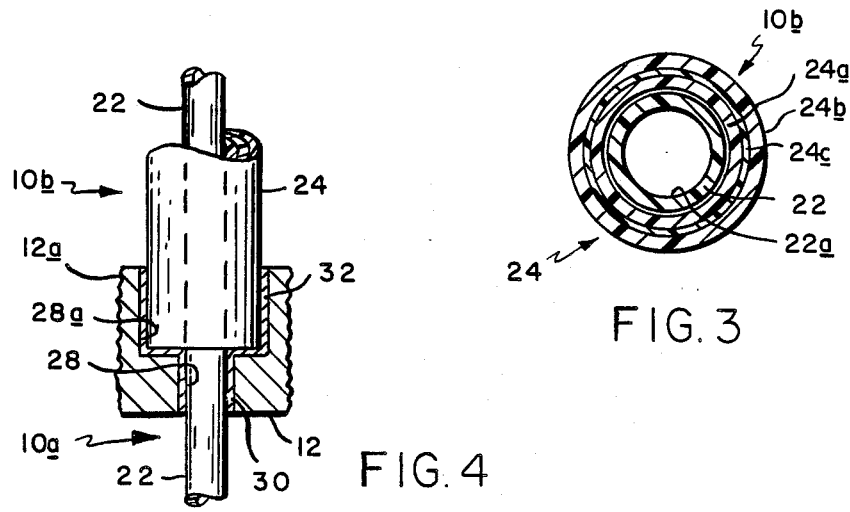
FIG. 3
FIG. 4

4,863,426

PERCUTANEOUS VENOUS CATHETER

This invention relates to catheters. It relates more particularly to a percutaneous central venous catheter which may be implanted in the human body to provide access to the venous system over an extended period of time.

BACKGROUND OF THE INVENTION

Intravenous infusion and removal of fluid from a person's body using a catheter have been widely practiced for many years. A venous catheter is a tubular member having a needle at its working end. The catheter is inserted into the patient's body by a puncture through the patient's skin to position the end of the catheter at the infusion site. The needle is then retracted, from the catheter, with the catheter remaining in the vasculature and exiting the body through the skin.

A length of catheter (usually flexible tubing) external to the body is then looped and taped to the patient's skin under a bandage. This warm environment is conducive to evaporation of fluid on the outside of the exterior segment of the catheter and it has been found that this evaporation tends to draw fluid from the inside of the catheter.

Apparently, this withdrawal of fluid is due to the fact that the materials of which conventional catheters are made, e.g. implant grade polyurethane or silicone, have high water vapor transmission rates. When evaporation occurs as aforesaid, transpiration occurs and water moves through the tubing wall of the external catheter segment to the relatively dry external environment. This phenomenon draws fluid up the catheter and simultaneously allows blood from inside the patient's body to move up the catheter. After a period of time, the catheter tip usually occludes due to a thrombus formation. This blockage necessitates removal and replacement of the catheter thereby increasing the patient's risk of infection. According to standard practice, venous catheters are normally flushed daily with a solution of sodium heparin or saline to maintain patency (prevent thrombus formation).

SUMMARY OF THE INVENTION

The present invention aims to provide an improved percutaneous venous catheter which can remain in the body for a relatively long period of time.

Another object of the invention is to provide a catheter of this type which is not prone to thrombus occlusion.

Yet another object of the invention is to provide a venous catheter which improves patient compliance by reducing the number of times required to access the catheter to maintain patency, thereby minimizing the patient's discomfort and risk of infection.

Other objects will in part be obvious and will in part appear hereinafter.

The invention accordingly comprises the features of construction, combination of elements and arrangement of parts which will be exemplified in the following detailed description, and the scope of the invention will be indicated in the claims.

Briefly, the catheter comprises a length of relatively small diameter flexible tubing made of a standard catheter material such as implant-grade polyurethane. The distal end of that tubing constitutes the catheter working end or tip which is designed to be implanted in the vasculature.

A cuff is bonded to that length of tubing for connecting the tubing to the extravascular segment of the catheter that extends outside of the body when the catheter is implanted in the body, that cuff being situated directly beneath the patient's skin.

That extravascular catheter segment is not simply a length of catheter tubing. Rather, it is a multilayer tubular structure consisting of a fluid-impervious sheath of a vapor barrier material coextruded between two layers of standard implant grade catheter tubing. The distal end of that plural ply catheter segment is connected to the wall of the catheter tubing by way of the cuff which establishes a fluid-tight seal with the tubing. The opposite or proximal end of the extravascular catheter segment is terminated by a standard Luer-lock connector.

When our catheter is implanted in the body with the cuff situated directly underneath the patient's skin, the vapor barrier present in the extravascular segment of the catheter minimizes the extent of fluid vapor transmission through the external wall of the catheter. Indeed, by choosing proper catheter wall thicknesses for a given material with a known water vapor transmission rate, the transpiration of fluid through the catheter wall can be adjusted so as to minimize fluid loss. By reducing water vapor transmission in this fashion, the movement of fluid, including blood, up the catheter is kept to a minimum so that there is reduced tendency for the catheter tip to become occluded due to a thrombus formation there. Resultantly, there is less need to access the catheter tip to maintain patency.

BRIEF DESCRIPTION OF THE DRAWING

For a fuller understanding of the nature and objects of the invention, reference should be had to the following detailed description, taken in connection with the accompanying drawing, in which:

FIG. 1 is an isometric view of a percutaneous venous catheter embodying our invention;

FIG. 2 is a sectional view on a larger scale taken along line 2—2 of FIG. 1;

FIG. 3 is a similar view taken along line 3—3 of FIG. 1; and

FIG. 4 is a fragmentary sectional view with parts in elevation showing a portion of FIG. 1 catheter in greater detail.

DESCRIPTION OF THE PREFERRED EMBODIMENT

Referring to FIG. 1 of the drawing, our catheter, shown generally at 10, includes an intravascular segment 10a that is arranged to be implanted in the body of a patient P and an extravascular segment 10b that extends outside the body. The boundary between the two segments 10a and 10b is defined by cuff 12.

When the catheter 10 is implanted as shown, the working end or tip 14 of the catheter is sutured into a selected blood vessel and the cuff 12 is positioned directly beneath the patient's skin S at an appropriate location in the body. Preferably, the cuff surface 12a is porous to permit fibrous ingrowth and thereby promote cuff fixation. The extravascular catheter segment 10b extends from cuff 12 and is terminated by a standard Luer-lock connector 16 by which the catheter 10 may be releasably coupled to an appropriate container. If the catheter is being used to administer a fluid to the patient, that container would contain an infusate. The length of catheter segments 10a and 10b are optional depending upon the location of the infusion site and the particular situation.

Catheter 10 may be inserted into the patient's body in the same way as any other conventional vascular catheter and the portion of the catheter segment 10b near the insertion site is, as usual, coiled and taped to the patient's skin S to minimize relative movement between the catheter and the patient P.

Referring to FIGS. 2 and 3, catheter segment 10a consists of a length of flexible tubing 22 made of a standard catheter material such as implant-grade polyurethane. The catheter tubing 22 has a central lumen 22a that leads to tip 14 and, as discussed at the outset, the tubing material is fluid pervious. However, since the exposed length of tubing 22 that constitutes catheter segment 10a is located inside the patient, it is surrounded by a fluid environment so that there is little or no transpiration of fluid through the tubing wall along segment 10a.

Catheter segment 10b could be an independent tubular member connected to tubing 22 by means of cuff 12. More preferably, however, to lend added strength to the catheter unit as a whole, the tubing 22 of catheter section 10a extends through cuff 12 and along the entire length of catheter section 10b. Thus, catheter segment 10b also includes a length of tubing 22. Surrounding that tubing is a flexible, fluid-impervious sleeve shown generally at 24. Sleeve 24 is basically also a flexible tube whose inner diameter is slightly larger than the outer diameter of tubing 22, thereby allowing tubing 22 to be threaded into the sleeve 24 as best seen in FIG. 3.

Sleeve 24 is actually a plural-ply tubular structure which includes an inner layer 24a composed of a standard implant-grade catheter tubing material, an outer layer 24b of the same material, and an intermediate vapor barrier layer 24c composed of a fluid impervious material such as polyolefin. In the catheter 10 embodiment specifically illustrated, the sleeve layers 24a to 24c are coextruded so that the sleeve 24 constitutes a unitary structure from end-to-end.

As shown in FIG. 4, cuff 12 is a cylindrical tubular member made of a biocompatible material such as polyester felt. The cuff includes a bore 28 at its lower end which is sized to snugly receive tubing 22. The wall of the cuff bore 28 is bonded at 30 to the outside wall of tubing 22 which, as mentioned above, is made of implant-grade polyurethane. The upper end of cuff 12 is recessed at 28a to snugly receive the lower end of sleeve 24 and an adhesive bond 32 is established between the wall of recess 28a and the outside wall of sleeve 24. Thus when the cuff 12 is bonded to tubing 22 and sleeve 24 as shown in FIG. 4, the cuff establishes a fluid-tight connection or seal between the lower end of sleeve 24 comprising catheter section 10b and the length of tubing 22 constituting catheter section 10a.

The upper ends of tubing 22 and sleeve 24 are located adjacent to one another and they both extend into and are bonded to the Luer-lock connector 16 as indicated in FIG. 1, so that the tubing lumen 22a forms a continuous fluid path from catheter tip 14 to connector 16.

Instead of forming sleeve 24 seperately from tubing 22 as depicted in the drawing, it could just as well be coextruded as a sheath directly onto the extravascular segment of tubing 22.

When catheter 10 is implanted as shown in FIG. 1, the segment 10a thereof beyond cuff 12 which remains in the vasculature is fluid pervious, but being maintained in a fluid environment, does not suffer transpiration. The extravascular catheter segment 10b is fluid impervious due to the presence therein of the vapor barrier layer 24c. Accordingly, there is minimal fluid transpiration through the wall of catheter segment 10b due to fluid evaporation from that segment. Since there is now no tendency for fluid or blood to move up the catheter lumen 22a promoting thrombus formation at the catheter tip 14, catheter 10 maintains its patency for a relatively long period of time. As a consequence, there is less need to remove the catheter from the patient so that the patient suffers less discomfort and risk of infection. As noted above, by choosing the proper wall thicknesses for sleeve 24, taking into consideration the materials which have a known water vapor transmission rate, the transpiration of fluid can be controlled or adjusted so as to minimize fluid loss through the catheter wall.

It will thus be seen that the objects set forth above, among those made apparent from the preceding description, are efficiently attained and, since certain changes may be made in the above construction without departing from the scope of the invention, it is intended that all matter contained in the above description or shown in the accompanying drawing be interpreted as illustrative and not in a limiting sense.

It is is also to be understood that the following claims are intended to cover all of the generic and specific features of the invention herein described.

What is claimed as new and desired to be secured by Letters Patent of the United States is:

1. A percutaneous catheter comprising
   A. a first catheter segment composed of a length of implant-grade vapor pervious catheter tubing and having an open tip;
   B. a second catheter segment including
      (1) a length of flexible tube composed of an implant-grade catheter tubing material, and
      (2) a vapor barrier sheath surrounding said tube;
   C. means for connecting one end of said second catheter segment in a fluid-tight manner to said first catheter segment tubing; and
   D. a connector fitting mounted to the opposite end of said second catheter segment, there being a continuous fluid path along said tube and tubing between said fitting and said tip.

2. The catheter defined in claim 1 wherein said second catheter segment tube is an integral extension of said first catheter segment tubing.

3. The catheter defined in claim 2 wherein said sheath is a flexible plastic sleeve connected between said connecting means and said fitting.

4. A percutaneous catheter comprising
   A. a first catheter segment composed of a length of implant-grade, vapor pervious, catheter tubing and having an open tip;
   B. a second catheter segment including
      1. a length of flexible tube composed of an implant-grade catheter tubing material, and
      2. a vapor barrier sheath surrounding said tube, said sheath being a flexible plastic sleeve connected between said connecting means and said fitting,
   said sleeve having a plural-ply wall comprising inner and outer plies of an implant-grade catheter tubing material and an intermediate ply of a water vapor imperious material.

5. The catheter defined in claim 4 wherein said sleeve is a coextrusion of said tubing and water vapor impervious materials.

6. The catheter defined in claim 5 wherein said tubing and said inner and outer sleeve plies are made of fluid-pefuious polyurethane or silicon and said intermediate ply is made of water vapor impervious polyolefin.

7. A percutaneous catheter comprising
   A. a first catheter segment of a length of implant-grade, vapor pervious, catheter tubing and having an open tip;
   B. a second catheter segment including
      1. a length of flexible tube composed of an implant-grade catheter tubing material and
      2. a vapor barrier sheath surrounding said tube;
   C. means for connecting one end of said second catheter segment in a fluid-tight manner to said first catheter segment tubing, said connecting means comprising
      1. a tubular cuff having an axial bore for snugly receiving said first catheter segment tubing at a selected location therealong and a larger diameter collinear counterbore for snugly receiving said second catheter one end; and
      2. means for bonding the walls at said bore and counterbore to said tubing and said second catheter segment one end, respectively.

8. The catheter defined in claim 7 wherein the outer wall of said cuff is porous.

* * * * *